US010015942B2

(12) United States Patent
de Jong et al.

(10) Patent No.: US 10,015,942 B2
(45) Date of Patent: Jul. 10, 2018

(54) **CYTOPLASMIC MALE STERILE *CICHORIUM* PLANTS**

(71) Applicant: Bejo Zaden B.V., Warmenhuizen (NL)

(72) Inventors: Elizabeth Rosalien de Jong, Heerhugowaard (NL); Adriana Dorien Haarsma, Middenmeer (NL); Witte Van Cappellen, Alkmaar (NL); Cornelis Glas, Tuitjenhorn (NL); Nicolaas Anthonius Zutt, Avenhorn (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 84 days.

(21) Appl. No.: 14/909,935

(22) PCT Filed: Aug. 14, 2013

(86) PCT No.: PCT/EP2013/067014
§ 371 (c)(1),
(2) Date: Feb. 3, 2016

(87) PCT Pub. No.: WO2015/022023
PCT Pub. Date: Feb. 19, 2015

(65) Prior Publication Data
US 2016/0165825 A1  Jun. 16, 2016

(51) Int. Cl.
| | |
|---|---|
| *A01H 5/12* | (2018.01) |
| *A01H 1/02* | (2006.01) |
| *C12N 5/14* | (2006.01) |
| *C12Q 1/68* | (2018.01) |
| *A01H 5/02* | (2018.01) |
| *A01H 1/00* | (2006.01) |
| *C12N 15/82* | (2006.01) |
| *C12Q 1/6895* | (2018.01) |

(52) U.S. Cl.
CPC .............. *A01H 5/025* (2013.01); *A01H 1/00* (2013.01); *A01H 5/12* (2013.01); *C12N 15/8289* (2013.01); *C12Q 1/6895* (2013.01); *A01H 1/02* (2013.01); *C12N 5/14* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 8,058,505 B2 *  11/2011  Horiuchi .................. A01H 5/12
435/419

FOREIGN PATENT DOCUMENTS

| EP | 1950290 | 7/2008 |
|---|---|---|
| NL | 1001554 | 8/1996 |
| WO | 1997045548 | 12/1997 |
| WO | 2007049730 | 5/2007 |
| WO | 2012163389 | 12/2012 |

OTHER PUBLICATIONS

Rambaud et al. Plant Breeding 116: 481-486 (1997).*
Dubreucq et al. Theoretical and Applied Genetics 99(7-8): 1094-1105 (1999).*
Varotto et al. Theoretical and Applied Genetics 102: 950-956 (2001).*
Nenz et al. Plant Cell, Tissue and Organ Culture 62: 85-88 (2000).*
Grazia et al. pp. 491-510 In: Biotechnology in Agriculture and Forestry, vol. 11, Y. Bajaj (ed.), Springer-Verlag: Berlin (1990).*
Briggs and Knowles (1967) "The Backcross Method of Breeding" Introduction to Plant Breeding, Reinhold Books in Agricultural Science, pp. 162-174.
Cappelle et al. (2007) "Regeneration and molecular characterization of a male sterile interspecific somatic hybrid between Cichorium intybus and C. endivia" Plant Science. 172(3)596-603.
Rambaud et al. (1993) "Male-Sterile Chicory Cybrids Obtained by Intergeneric Protoplast Fusion" Theoretical and Applied Genetics. 87:347-352.
Zhao et al. (2011) Database EMBL "TSA: Lactuca serriola Serrassy_T_P2_40555 mRNA sequence." Accession No. JO047151.
Zhao et al. (2011) Database EMBL "TSA: Lactuca serriola Serrassy_T_P2_52008 mRNA sequence." Accession No. JO058801.

* cited by examiner

*Primary Examiner* — David T Fox
(74) *Attorney, Agent, or Firm* — Edward J. Baba; Bozicevic Field & Francis LLP

(57) ABSTRACT

The present invention relates to cytoplasmic male sterile (CMS) *Cichorium* plants and especially to cytoplasmic male sterile (CMS) green chicory plants; cytoplasmic male sterile (CMS) radicchio rosso plants; cytoplasmic male sterile (CMS) red leaved chicory plants, cytoplasmic male sterile (CMS) Treviso plants, cytoplasmic male sterile (CMS) white chicory plants, cytoplasmic male sterile (CMS) sugar loaf plants, cytoplasmic male sterile (CMS) Belgian endive plants, cytoplasmic male sterile (CMS) witloof plants, cytoplasmic male sterile (CMS) Catalogna plants, cytoplasmic male sterile (CMS) *C. intybus* var. *foliosum* plants, cytoplasmic male sterile (CMS) *C. endivia* plants and cytoplasmic male sterile (CMS) *C. intybus* L. var. *sativum* plants. The present invention further relates to methods for identifying cytoplasmic male sterile (CMS) *Cichorium* plants and mitochondrial nucleic acid sequences providing cytoplasmic male sterility (CMS) in *Cichorium* plants.

4 Claims, 8 Drawing Sheets

```
                             SEQUENCE LISTING

<160> NUMBER OF SEQ ID NOS: 38

<210> SEQ ID NO 1
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 1
ccgaaccgcg cgaaatggtc gcctattaca cggctcacta actctgcctg gagtggtggt      60
acctattatt cgtcggcggg ggcggtccgg cgatac                               96

<210> SEQ ID NO 2
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 2
ctcttaaggt tagttctatg cctcacaaca actacctcat aggtgattct aaatccgtct      60
ttagatcaga agtagatgcc tcttccaggg ctctgt                               96

<210> SEQ ID NO 3
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 3
gtaccaaatg cttggcaatc cttggtagag cttatttatg atttcgtgct taacctggta      60
aacgaacaaa taggggtct ttccggaaat gttaaa                                96

<210> SEQ ID NO 4
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
```

/organism="Lactuca"

<400> SEQUENCE: 4
tattgattac actccttctc ctactgcttc tccttatacc cactaatgtt cttcttcgtc    60
ctaccttgac tattgggaaa tttccattcg agaaag                              96

<210> SEQ ID NO 5
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 5
tgcagcgtaa actcctgcta aatgaatgcc tttgctttgg ctttgaaatt atgttcctga    60
ttcaactcct tcatgccatt gattgatgca agtctt                              96

<210> SEQ ID NO 6
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 6
ctgaatgacc tctctcatct aatcgatcgg tgaaggatgt ctttgaagat aatctggtct    60
ggctcgttac cattagttcc tctctctata gtcgag                              96

<210> SEQ ID NO 7
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 7
ctcttgttct cttttcttag ttaggcccaa gaaagtacaa gatatagctt gactaatata    60
ctaagatgat agctagagac tagagatgag agtgca                              96

<210> SEQ ID NO 8
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 8
ttggatattg tacgacagga tccccatccg tgttttcgtt tcgctaacga gaaaggccgg    60
aaagcgtggg acctatttaa gtgacctggc cgatgg                              96

<210> SEQ ID NO 9
<211> LENGTH: 96

```
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 9 ttttcgttc cttctcttcg ataagaatat cgatttgaaa tgataaaaat gcctctttat    60
tctcttgtgc tcagcgaaag aactgcctaa gcatac                             96

<210> SEQ ID NO 10
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 10
gtccgatcgt cgctagaggc ccgtcgacta taatacactg ttcgaaattt attcgtttct    60
gccgaaacaa aacgggattg gctatcttaa ccttag                             96

<210> SEQ ID NO 11
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 11
aaggaaatga tctttacatg gaaatgaaag aatctggagt aattaatgaa maaaatattc    60
cagaatcaaa agtagctcta gtttacggtc agatga                             96

<210> SEQ ID NO 12
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 12
ggggcgtcca aagagtcgat catttctgca tgatttttt ctcgtgcact rccccttcca    60
atgggtttcg aagataaaaa tcctttattg gcccat                             96

<210> SEQ ID NO 13
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 13
catacgctaa aatttgtccc tttttaatgc atttaccccg ctgaacctgg rgttttgat     60
```
gcatacaagt atttttgttg gaacgttgat acataa                                    96

<210> SEQ ID NO 14
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 14
agataaaaat aacaaggaat agaatttgat tagttggtat tcaaaatata ygattcaagt          60
agtcaagtcg agaaagagat ggttgaatca aaataa                                    96

<210> SEQ ID NO 15
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 15
taagcaatat attgattttc ttctccagga acaggctcga ttccatagca kcgccctttg          60
taacgatcaa ggctcgtaag tccatcggtc cacaca                                    96

<210> SEQ ID NO 16
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 16
acttttattt ggcattggaa gcacattaca ttatggcagg gtaatgtttc rcagtttaat          60
gaatcttcca cttatttgat gggctggtta agagat                                    96

<210> SEQ ID NO 17
<211> LENGTH: 96
<212> TYPE: DNA
<213> ORGANISM: Lactuca
<220> FEATURE:
<221> NAME/KEY: source
<222> LOCATION: 1..96
<223> OTHER INFORMATION: /mol_type="DNA"
      /organism="Lactuca"

<400> SEQUENCE: 17
ggtatgaata gtttatcagt ctgggcatgg atgtttttat ttggacatct kgtttgggct          60
actggattta tgtttttaat ttcctggcgt ggatat                                    96

<210> SEQ ID NO 18
<211> LENGTH: 96
<212> TYPE: DNA
<213> ORGANISM: Cichorium
<220> FEATURE:
<221> NAME/KEY: source
<222> LOCATION: 1..96

```
<223> OTHER INFORMATION: /mol_type="DNA"
      /organism="Cichorium"

<400> SEQUENCE: 18
ccgaaccgcg cgaaatggtc gcctattaca cggctcacta actctgcctg tagtggtggt    60
acctattatt cgtcggcggg ggcggtccgg cgatac                              96

<210> SEQ ID NO 19
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 19
ctcttaaggt tagttctatg cctcacaaca actacctcat aggtgattct caatccgtct    60
ttagatcaga agtagatgcc tcttccaggg ctctgt                              96

<210> SEQ ID NO 20
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 20
gtaccaaatg cttggcaatc cttggtagag cttatttatg atttcgtgct gaacctggta    60
aacgaacaaa taggggtct ttccggaaat gttaaa                               96

<210> SEQ ID NO 21
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 21
tattgattac actccttctc ctactgcttc tccttatacc cactaatgtt attcttcgtc    60
ctaccttgac tattgggaaa tttccattcg agaaag                              96

<210> SEQ ID NO 22
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 22
tgcagcgtaa actcctgcta aatgaatgcc tttgctttgg ctttgaaatt ctgttcctga    60
ttcaactcct tcatgccatt gattgatgca agtctt                              96

<210> SEQ ID NO 23
```

<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 23
ctgaatgacc tctctcatct aatcgatcgg tgaaggatgt ctttgaagat catctggtct      60
ggctcgttac cattagttcc tctctctata gtcgag                                96

<210> SEQ ID NO 24
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 24
ctcttgttct cttttcttag ttaggcccaa gaaagtacaa gatatagctt tactaatata      60
ctaagatgat agctagagac tagagatgag agtgca                                96

<210> SEQ ID NO 25

<400> SEQUENCE: 25

000

<210> SEQ ID NO 26
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 26
ttggatattg tacgacagga tccccatccg tgttttcgtt tcgctaacga taaaggccgg      60
aaagcgtggg acctatttaa gtgacctggc cgatgg                                96

<210> SEQ ID NO 27
<211> LENGTH: 96
<212> TYPE: DNA
<213> ORGANISM: Cichorium
<220> FEATURE:
<221> NAME/KEY: source
<222> LOCATION: 1..96
<223> OTHER INFORMATION: /mol_type="DNA"
      /organism="Cichorium"

<400> SEQUENCE: 27
tttttcgttc cttctcttcg ataagaatat cgatttgaaa tgataaaaat tcctctttat      60
tctcttgtgc tcagcgaaag aactgcctaa gcatac                                96

<210> SEQ ID NO 28
<211> LENGTH: 96
<212> TYPE: DNA
<213> ORGANISM: Cichorium
<220> FEATURE:

```
<221> NAME/KEY: source
<222> LOCATION: 1..96
<223> OTHER INFORMATION: /mol_type="DNA"
      /organism="Cichorium"

<400> SEQUENCE: 28
gtccgatcgt cgctagaggc ccgtcgacta taatacactg ttcgaaattt cttcgtttct    60
gccgaaacaa aacgggattg gctatcttaa ccttag    96

<210> SEQ ID NO 29
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 29
gcctccaggg tatgatcctt aa    22

<210> SEQ ID NO 30
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 30
cgagcactta tttgacctgt gt    22

<210> SEQ ID NO 31
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 31
tgctaacgag gttcaatgat g    21

<210> SEQ ID NO 32
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 32
ttcgattcag gatcaagccc ag    22

<210> SEQ ID NO 33
<211> LENGTH: 22
<212> TYPE: DNA
```

```
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 33
tcgatattct tttcgcgaca gg                                              22

<210> SEQ ID NO 34
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 34
ttaggttatt tcgttggtcg cc                                              22

<210> SEQ ID NO 35
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 35
tttatagaca gcgactccct cc                                              22

<210> SEQ ID NO 36
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 36
acctgaaggg agttatggca tt                                              22

<210> SEQ ID NO 37
<211> LENGTH: 10
<212> TYPE: DNA
<213> ORGANISM: artificial sequences
<220> FEATURE:
<221> NAME/KEY: source
<222> LOCATION: 1..10
<223> OTHER INFORMATION: /mol_type="DNA"
      /note="RAPD primer"
      /organism="artificial sequences"

<400> SEQUENCE: 37
agtcgggtgg                                                            10

<210> SEQ ID NO 38
<211> LENGTH: 16
```

```
<212> TYPE: DNA
<213> ORGANISM: artificial sequences
<220> FEATURE:
<221> NAME/KEY: source
<222> LOCATION: 1..16
<223> OTHER INFORMATION: /mol_type="DNA"
      /note="iSSR primer"
      /organism="artificial sequences"

<400> SEQUENCE: 38
ccaggtgtgt gtgtgt                                                     16
```

CYTOPLASMIC MALE STERILE *CICHORIUM* PLANTS

Figure 1A:
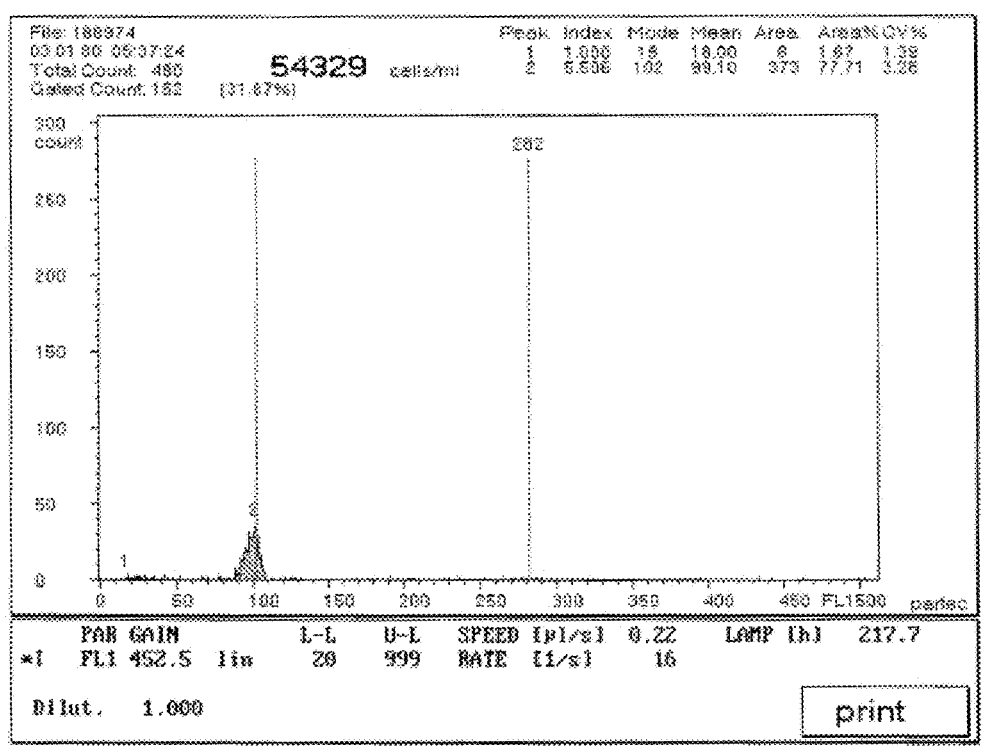

The present invention relates to cytoplasmic male sterile (CMS) *Cichorium* plants and especially to cytoplasmic male sterile (CMS) green chicory plants; cytoplasmic male sterile (CMS) radicchio rosso plants; cytoplasmic male sterile (CMS) red leaved chicory plants, cytoplasmic male sterile (CMS) Treviso plants, cytoplasmic male sterile (CMS) sugar loaf plants, cytoplasmic male sterile (CMS) white chicory plants, cytoplasmic male sterile (CMS) Belgian endive plants, cytoplasmic male sterile (CMS) witloof plants, cytoplasmic male sterile (CMS) Catalogna plants, cytoplasmic male sterile (CMS) endive plants, cytoplasmic male sterile (CMS) *C. intybus* var. *foliosum* plants, cytoplasmic male sterile (CMS) *C. endivia* plants and cytoplasmic male sterile (CMS) *C. intybus* L. var. *sativum* plants. The present invention further relates to methods for identifying cytoplasmic male sterile (CMS) *Cichorium* plants and mitochondrial nucleic acid sequences providing cytoplasmic male sterility (CMS) in *Cichorium* plants.

*Cichorium* is available in several distinct cultivated forms: as green chicory, radicchio rosso or red leaved chicory, Treviso, white chicory, sugar loaf, Belgian endive (witloof), Catalogna (all *C. intybus* var. *foliosum*), endive (*C. endivia*) but also root chicory (*C. intybus* L. var. *sativum*) is known. The latter is cultivated for its taproot from which several products as inulin, flavour for beer, coffee substitutes but also substrates for polymer production are derived.

Witloof is grown for its taproot initially, which then is forced in the dark to produce the well-known witloof, Belgian endive or chicon. This forcing is done hydroponically or conventionally.

Examples of leaf chicories (*Cichorium intybus* var. *foliosum*) are radicchio rosso (with variegated red and green leaves, sometimes with white veins), Treviso, Catalogna and green hearted chicory. Typical for all chicory varieties is the somewhat bitter taste. Another member of the Cichorieae is endive, *Cichorium endivia*.

The Cichoriae are part of the Asteraceae (formerly Compositae) to which, among others, belong sunflower (*Helianthus*), lettuce (*Lactuca*), *Calendula, Aster* and *Echinacea*.

Using the present state of the art for commercially available *Cichorium* seeds (like radicchio rosso, Treviso and others) hybrids are produced using certation.

Certation is the botanical phenomenon where there is competition between pollen tubes, showing a difference in growth rate. Pollen tubes of the same plant (self-pollination) grow slower through the style then pollen tubes of another, cross-pollinating plant. This mechanism is exploited to enhance the share of cross-fertilization but self-fertilization, resulting in impurity of the desired hybrid, cannot be excluded. In practice up to 30% of the produced seed consists of products of self-fertilization, in other words, inbred plants instead of hybrid plants. Using seed cleaning methods, this percentage can be reduced to 10-20% but is still undesirably high.

An additional drawback of using certation is that during maintenance of the female line (having certation), individual plants yielding more pollen spread their genes in the population more efficiently resulting in potential loss of certation after a number of generations, i.e. an useless parental line.

Further, certation is not present in all lines of *Cichorium*, thus reducing the combination possibilities to produce commercially interesting hybrids.

For the culture of chicory in all the described forms above, it will therefore be advantageous to have highly, preferably substantially 100%, uniform F1 hybrids available. These hybrid *Cichorium* varieties have several advantages over the now common available races.

The most important advantage is the superb uniformity such a F1 hybrid will offer, i.e. substantially 100% uniformity. This enables a harvest that can be performed at one time or simultaneously, in addition to resulting in a minimal loss after sorting the crop.

For example, radicchio rosso gets less intense in color as the crop is exposed to high temperatures and intense daylight for prolonged times. The possibility to simultaneously harvest this product results in a reduction of loss for the grower.

When the *Cichorium* plant is highly or substantially 100% uniform with respect to the genetic composition, i.e. genome, of the *Cichorium* plant, there are several advantages, both for a producer of seeds and the grower of the crop.

When a highly uniform F1 hybrid can be provided, the producer has the advantage that more combinations of parent lines can be used, resulting in a broader range of available hybrids.

Presently, seed treatment as priming and the like or seed selection are of little use since uniformity in the seed lots is too low. When the high quality seeds of the desired highly uniform hybrid are available, processes like priming and other seed-technological treatments of the seeds become useful.

For the grower, advantages of a highly uniform hybrid are a short period for harvesting and processing the total crop, consisting of a very homogenous product without so-called off-types. For this reason, less labor is required to harvest the crop and prepare it for sale.

A highly or substantially 100% uniform hybrid has a consistent quality, especially for color when considering e.g. radicchio rosso. The varieties available on the market now cannot guarantee this consistent quality.

Finally, it can be noted that highly uniform F1 hybrids will show a better emergence of the seeds.

For *Cichorium endivia* (endive) production of hybrids with the current state of the art is impossible; a mechanism as certation is not present in endive. Therefore endive is 100% self-pollinating crop, albeit showing a high level of uniformity it has a poor heterosis.

To improve on the aforementioned points much research is performed to develop other methods for hybridization in *Cichorium*. One of the methods is described in patent applications made by Enza Zaden (NL 1001554) and Florimond Desprez (WO 97/45548) where a cytoplasmic factor from sunflower (*Helianthus annuus*) is introduced by cell fusion in *Cichorium* species. This resulted in cytoplasmic male sterile (CMS) *Cichorium* breeding material. A similar patent application is submitted by Sakata Seeds as WO 2007/049730 where CMS from sunflower is transferred into lettuce, *Lactuca sativa*.

Yet another approach is described in patent application WO 2012/163389 by Az. Agricola T&T, where a recessive or genetically nuclear encoded male sterility is induced in *Cichorium* by mutagenesis. F1 hybrids produced with this system are, due to the recessive character of the described trait, male fertile. A further draw-back of this system is that male sterile mother lines (denoted as ms/ms) have to be propagated vegetatively by in vitro or in vivo methods.

Considering the above, it is an object of the present invention, amongst other objects, to provide cytoplasmic male sterile *Cichorium* plants obviating the above drawbacks of the prior art.

The above object, amongst other objects, has been met by the present invention, by providing plants as described in the appended claims.

Specifically, the above object, amongst other objects, has been met by the present invention, according to a first aspect, by cytoplasmic male sterile *Cichorium* plants comprising mitochondria of *Lactuca*, wherein said mitochondria of *Lactuca* comprise at least one mitochondrial nucleic acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and SEQ ID No. 10.

A research program was initiated to identify plant species which might serve as a suitable donor for the introduction of cytoplasmic male sterility (CMS) in *Cichorium*. In this context, "suitable" also means that the disadvantages of the prior art are obviated.

In lettuce, *Lactuca* sp., no CMS is present. *Lactuca* and *Cichorium* belong to the family of the Asteraceae and within this family to the tribe Cichorieae or Lactuceae, respectively.

The combination *Lactuca* and *Cichorium* was studied to determine whether a combination of *Cichorium* nuclei with the cytoplasm of *Lactuca* would result in a cytoplasmic male sterile (CMS) *Cichorium*.

In lettuce, *Lactuca* sp., no CMS is present. *Lactuca* is related to *Cichorium*, both belong to the family of the Asteraceae and within this family to the tribe Cichorieae or Lactuceae; therefore this plant was chosen as a candidate both for crosses and asymmetric cell fusions with *Cichorium*.

With the *Lactuca* mentioned above, the combination with *Cichorium* was studied to determine whether a combination of *Cichorium* nuclei with the cytoplasm of *Lactuca* would result in a cytoplasmic male sterile *Cichorium*. This research was aimed especially at several *Lactuca* species since initial research learned that crossing of *Cichorium* with *Lactuca* resulted in a-limited-amount of seeds. Plants grown from these seeds were recognized as hybrid both by flowcytometrical as molecular studies.

After obtaining this hybrid between *Cichorium* and *Lactuca* it will be necessary to perform several backcrosses to regain the genetic setup of *Cichorium*. With a crop like *Cichorium* it will take at least 8 years to reconstruct the complete genome of this species in the product of the crossings. Next to that, a cross between distinct species is very inefficient, especially in the first generations, so the amount of seeds yielded will be very limited initially.

After several generations the amount of *Lactuca* genome is diluted sufficiently but an inbred generation, made by self-pollination, is required to select the required genetically stable candidate parent line for hybrid production. However, since this material will be male sterile, this final self-pollination step is impossible.

To provide a solution to the drawbacks mentioned before Bejo Zaden B.V. performed asymmetric cell fusions between *Cichorium* species and *Lactuca* sp.

Briefly, protoplasts from both species were isolated. Protoplasts from *Cichorium* (the acceptor) were treated with iodoacetamide (IOA) or iodoacetate (IA) for inactivation of the cytoplasm. Protoplasts of *Lactuca* sp. (the donor) were treated with ionizing radiation to inactivate or destroy the nuclear genome but maintaining active genetic elements in the cytoplasm (chloroplasts and mitochondria).

After a PEG/$Ca^{2+}$ mediated cell fusion, one or more novel cells are formed with the nuclear genome (and thus horticultural characteristics) of *Cichorium* but with the cytoplasm of *Lactuca*. This fusion can be performed either in test tubes or petri dishes. Here PEG acts as a means to promote the association of cells, a high pH and $Ca^{2+}$ ions are a prerequisite for the actual fusion of cells. A FDA staining procedure is used to ascertain the resulting cells are viable.

A suitable medium comprising water, salts, vitamins, sugars and plant hormones was used to promote the formation of calli. Subsequently, the regeneration of plants was performed by promoting the advent of shoots which finally are rooted; also these stages are dependent of the application of suitable plant hormones.

After regeneration, the plants obtained are checked for a correct DNA content using flowcytometry. Diploid plants resulting from this check then are subject to a molecular test to ascertain the presence of the *Lactuca* cytoplasm. To this end a RAMP technique was used to discriminate between the *Cichorium* and *Lactuca* cytoplasm.

Further research on plants containing the *Cichorium* nuclear material combined with the *Lactuca* cytoplasm showed that between the regenerated fusion plants, individual plants occur which are male sterile while retaining female fertility, i.e. plants according to the present invention. The frequency with which these plants were identified was about 1 in 21 original fusion plants.

The plant obtained had flowers with visible pollen grains on the anthers but these are smaller than wild type pollen grains and using a FDA staining technique, it was shown that pollen of the hybrid plant were not viable. Accordingly, the F1 hybrid plants are male sterile. Thus, from the above fusion plants, the present *Cichorium* plants are obtained which are suitable to produce 100% pure hybrids of *Cichorium*.

A representative sample of a plant according to the present invention was deposited on Mar. 12, 2013 at NCIMB Ltd, Ferguson Building, Craibstone Estate, Bucksburn, Aberdeen, AB21 9YA, UK with deposit number NCIMB 42125.

According to a preferred embodiment of this first aspect, the present invention relates to cytoplasmic male sterile *Cichorium* plants, wherein the cytoplasmic male sterile *Cichorium* plants are further identifiable by a molecular marker of 1592 bp using SEQ ID No. 31 and SEQ ID No. 32.

According to another preferred embodiment of this first aspect, the present invention relates to cytoplasmic male sterile *Cichorium* plants, wherein the cytoplasmic male sterile *Cichorium* plants are further identifiable by a molecular marker of 293 bp using SEQ ID No. 33 and SEQ ID No. 34.

According to an especially preferred embodiment, the present invention relates to cytoplasmic male sterile *Cichorium* plants having at least two, at least three, at least four, at least five, at least six, at least seven, at least eight, at least nine, or ten of the present mitochondrial nucleic acid sequences.

The plants according to the present invention are preferably selected from the group consisting of green chicory, radicchio rosso, red leaved chicory, Treviso, white chicory, sugar loaf, Belgian endive, witloof, Catalogna, *C. intybus* var. *foliosum, C. endivia*, and *C. intybus* L. var. *sativum*.

According to most preferred embodiments of the present invention, the present plants comprise *Lactuca* mitochondria derived from a plant according to deposit NCIMB 41985 and/or the present plants comprise a cytoplasm maternally derived from a plant according to deposit NCIMB 42125.

According to a second aspect, the present invention relates to methods for identifying a cytoplasmic male sterile *Cichorium* plant, the method comprises establishing in a sample of said cytoplasmic male sterile *Cichorium* plant one or more of the present mitochondrial sequences, i.e. nucleic acid sequences selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and SEQ ID No. 10.

According to a third aspect, the present invention relates to methods for identifying a cytoplasmic male sterile *Cichorium* plant, the method comprises establishing in a sample of said cytoplasmic male sterile *Cichorium* plant a molecular marker of 1592 bp using nucleic acid amplification primers SEQ ID No. 31 and SEQ ID No. 32 and/or a molecular marker of 293 bp using nucleic acid amplification markers SEQ ID No. 33 and SEQ ID No. 34.

According to a fourth aspect, the present invention relates to mitochondrial nucleic acid sequences selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, and SEQ ID No. 17.

According to a fifth aspect, the present invention relates to cytoplasmic male sterile hybrid plants of *Cichorium* and *Lactuca*, wherein the cytoplasmic male sterile hybrid plants comprise mitochondria of *Lactuca* and said mitochondria comprise at least one mitochondrial nucleic acid sequence selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, and SEQ ID No. 10.

According to a preferred embodiment of this fifth aspect of the present invention, the present cytoplasmic male sterile hybrid plants are a cytoplasmic male sterile hybrid plant according to deposit NCIMB 42125 and/or comprise mitochondria derived from a *Lactuca* plant according to deposit NCIMB 41985.

According to a sixth aspect, the present invention relates to the use of mitochondria of a *Lactuca* plant for obtaining a cytoplasmic male sterile *Cichorium* plant, the present use preferably comprises a protoplast fusion of a nuclear genome inactivated protoplast of *Lactuca* as donor and a mitochondrial genome inactivated protoplast of *Cichorium* as acceptor.

Figure 1B:
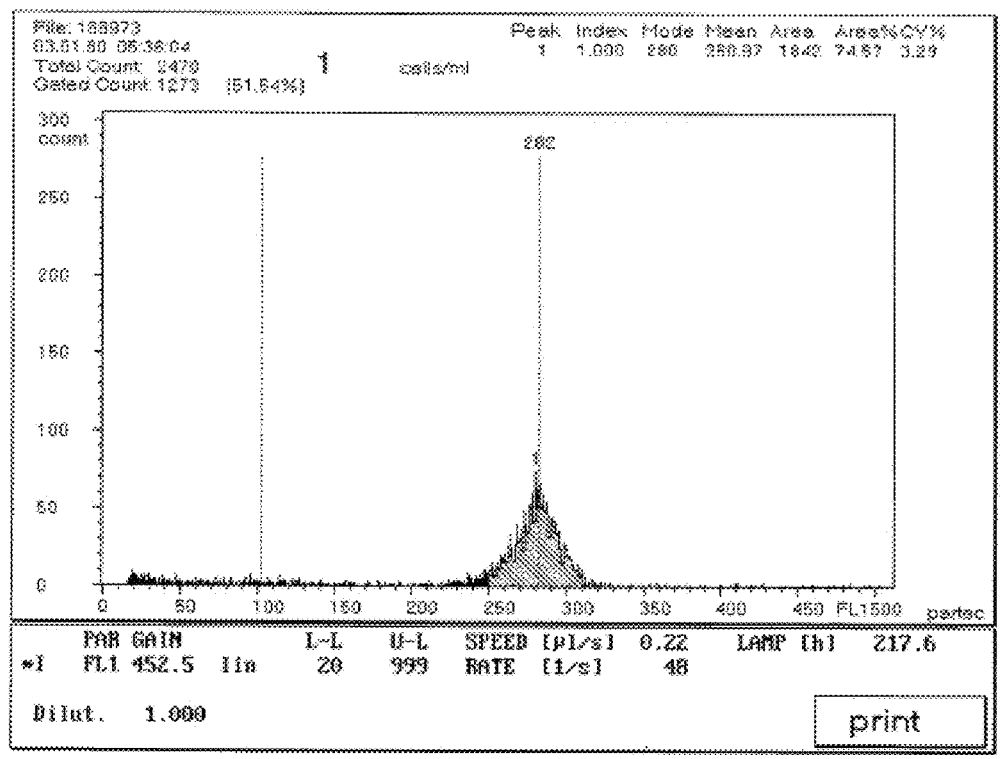
Figure 1C:
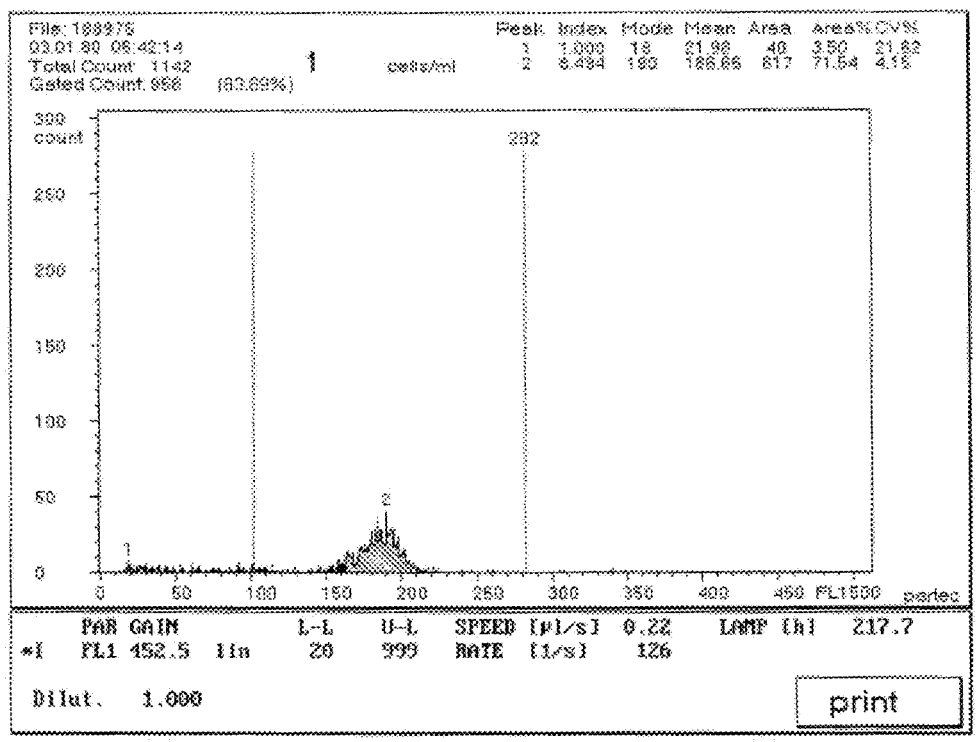
Figure 1D:
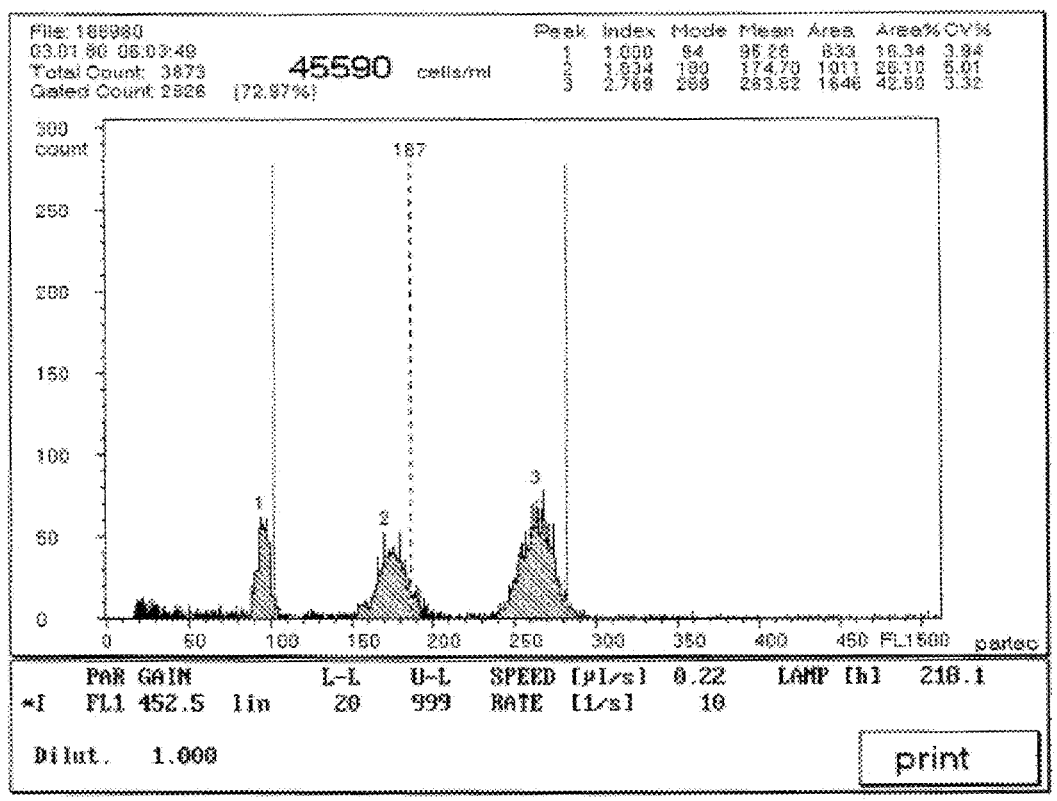
Figure 2:
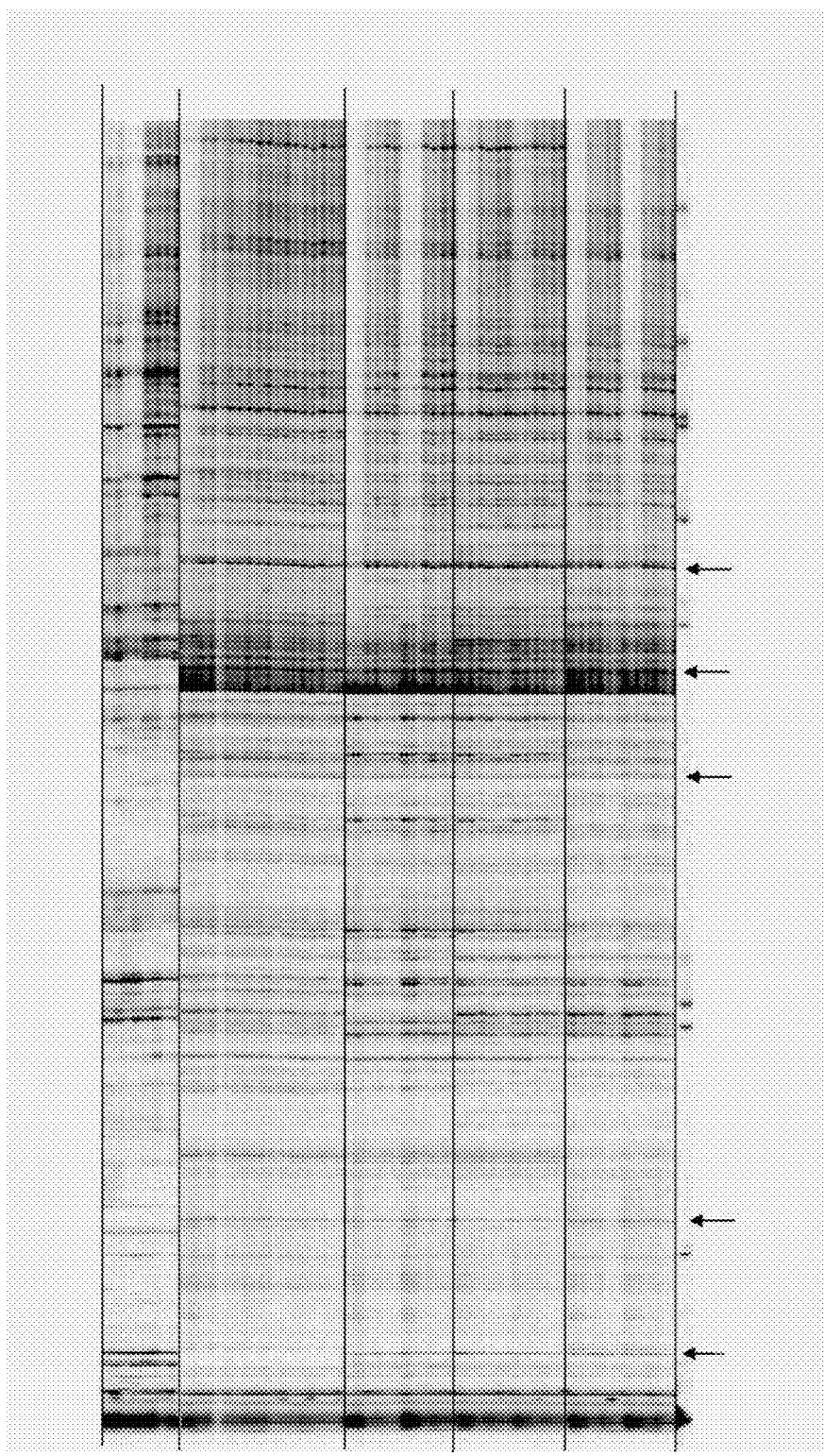
Figure 3:
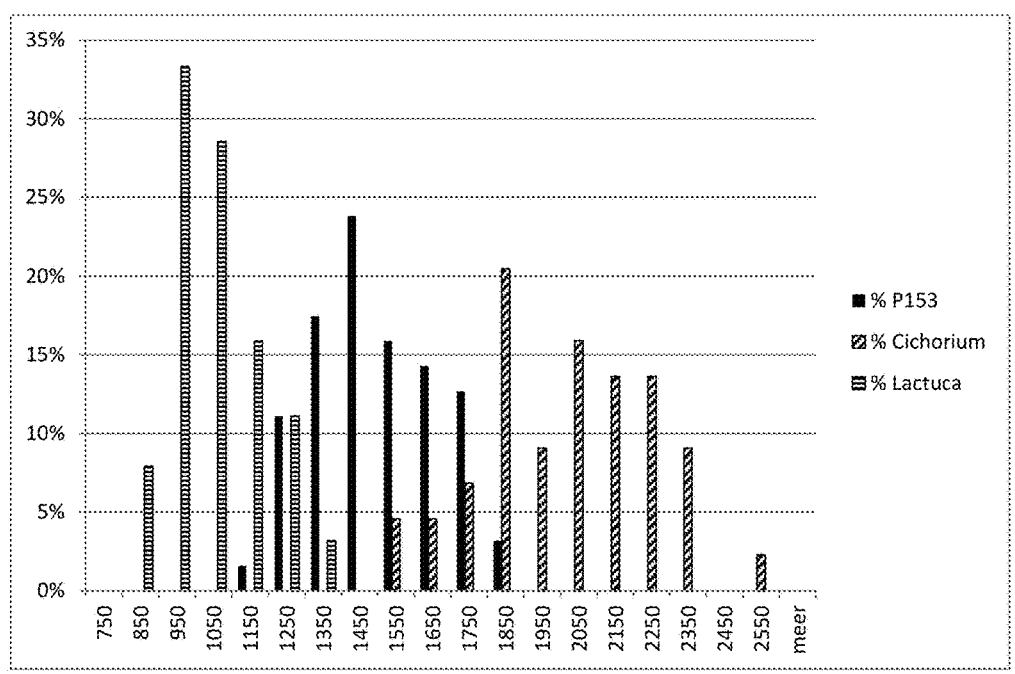
Figure 4:
Figure 4:
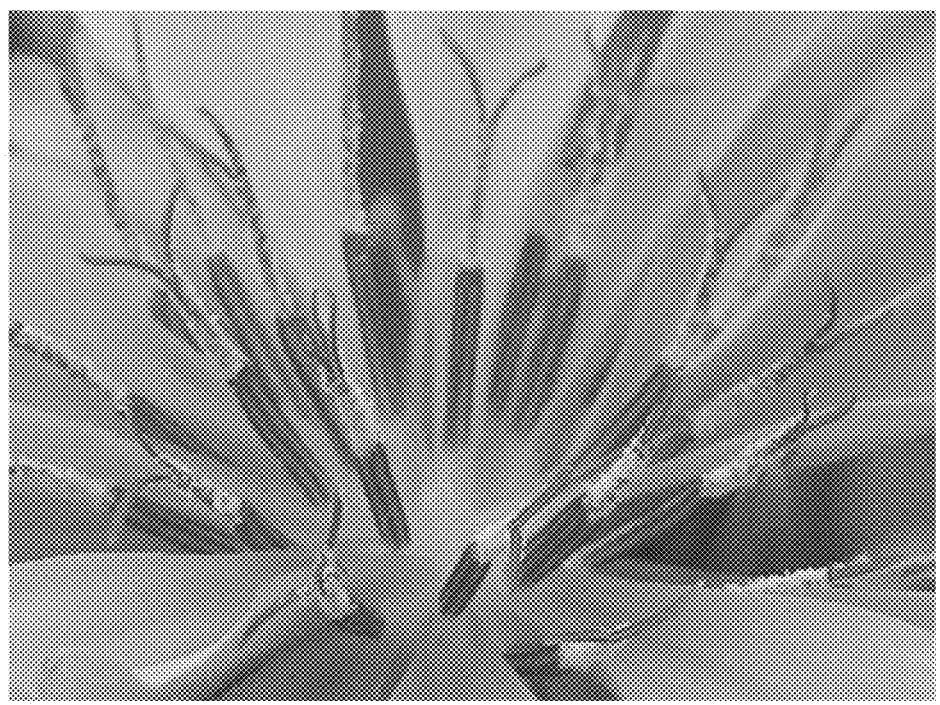
Figure 5:

Below, the present invention will further be described in examples of preferred embodiments of the present invention. In the examples, reference is made to figures wherein:

FIGS. 1A-1D: show flowcytograms of: *Cichorium intybus* L. (FIG. 1A); *Lactuca* sp. (FIG. 1B); Hybrid 1 (according to the present invention; FIG. 1C); and a mixed sample of *Cichorium intybus* L., *Lactuca* sp., and Hybrid 1 (FIG. 1D);

FIG. 2: shows result of a molecular characterization of nuclear DNA using the RAMP technique. From left lane to right lane, *Cichorium intybus* (P155); *Lactuca* sp. (P157); hybrids 1 to 3 (H1-H3, i.e. hybrid plants of a cross between P155 and P157; discriminating bands are indicated;

FIG. 3: shows a graphic representation of pollen size of *Cichorium*, *Lactuca* and the selected fusion plant P153. Legend to this graph:
 X axis: diameter of pollen grains in μm2
 Y axis: percentage of pollen grains present in the distinct sizes;

FIG. 4: shows TOP: Photograph of a flower of P153, a selected plant from the described fusion products obtained. BOTTOM: detail of the anthers showing (non-functional) pollen grains;

FIG. 5: shows TOP: Photograph of a fertile flower of *Cichorium intybus* L. BOTTOM: detail of the anthers.

EXAMPLES

Example 1

Sterilization and Sowing of Seeds

Seeds from both the donor (*Lactuca* sp., deposited on Jun. 1, 2012 at NCIMB Ltd, Ferguson Building, Craibstone Estate, Bucksburn, Aberdeen, AB21 9YA, UK as deposit NCIMB 41985, and the acceptor (*Cichorium intybus* L.) were sown in vitro. To this end 100 seeds of each species were sterilized by a rinse in 70% ethanol in water, succeeded by a treatment with a bleach solution (1% (w/v) NaOCl+ 0.01% (v/v) Tween80 in demineralized water). After a thorough rinse with sterile demineralized water, seeds were placed on a suitable medium as ½MS15 and placed in a growth room at 25° C., 16/24 hrs. light. After 4 weeks plants were suitable for protoplast isolation.

Example 2

Isolation of Protoplasts

Young, surface-sterilized leaves of 4 week old plants were collected. These leaves were cut in pieces of 1-2 mm in TC quality petri dishes (Greiner Bio-One, article 664160) in plasmolysing solution WS9M. After collecting all material, this solution was replaced by 20 ml of enzyme solution containing cell wall degrading enzymes like pectinase and/ or cellulase. After an overnight incubation (dark, 25° C.) on an orbital shaker with a speed of 30 rpm, material was sieved on respectively a 110 and a 53 μm filter; these filters were rinsed twice with 10 ml wash solution.

The collected filtrate was centrifuged for 5 minutes at 60× g. After resuspending the pellet in 10 ml wash solution, this centrifugation step was repeated. Protoplasts were kept on ice until further processing.

Example 3

Viability Control

A check for viability of the isolated protoplasts and pollen grains was performed with FDA. To this end, samples of stained protoplasts, from both donor and acceptor, or pollen grains collected from donor or selected fusion plants, were checked with a fluorescence-microscope using the appropriate filters, magnification 10×.

Viable cells can be recognized by a bright yellow-green color, non-viable cells do not fluoresce.

Example 4

Pretreatment of Isolated Protoplasts

Isolated protoplasts from the donor (*Lactuca*) were treated with a suitable source of ionizing radiation (e.g. a source of Roentgen or gamma radiation). A suitable dose is in the range of 250-500 Gray as measure of absorbed energy. From the protoplasts isolated from the acceptor (*Cichorium intybus* var. *foliosum*), cellular organelles were inactivated by a treatment with a final concentration IOA of 10 mM (supplied from a 60 mM IOA stock solution) during 10 minutes at 4°

C. After this treatment cells were washed twice with wash solution and centrifuged at 60×g during 5 minutes.

Fusion and successive regeneration of the protoplasts obtained can be performed in two alternative ways as described in the examples 5 and 6a (culture in liquid medium) and 5 and 6b (embedded in solid medium using sodium alginate) respectively.

Example 5

Fusion of Protoplasts

Per 10 ml tube (round bottom, Greiner, catalogue number 163189) $1\times10^6$ protoplasts (in a ratio of acceptor:donor of 1:1 or 2:1) in wash solution were added.

After centrifugation (5 minutes at 60*g) each pellet was resuspended in 0.3 ml wash solution. Then, 0.4 ml PEG1500 solution per test tube was added by letting separate drops fall into the tubes; no further mixing was allowed here. After standing still for 30 minutes, 0.8 ml PEG diluting solution was added, by slowly flowing down the test tube wall. Without further mixing the cells are left for 10 minutes.

After this, tubes are topped up with CPW-$Ca^{++}$ solution to a final volume of 10 ml, without further mixing the cells are centrifuged for 5 minutes at 60*g. After three repetitive washing with CPW-$Ca^{++}$ solution pellets were resuspended in PM1 culture medium providing a final density of 20.000 protoplasts/ml.

Example 6

Culture of Fused Protoplasts

Example 6a

Using Liquid Regeneration Media

Culturing was performed in dark at 25° C., every week the culture medium is partly replaced:
  6 cm dish: 3 ml (out of 4.5 ml) is replaced by 3 ml fresh PM1 medium
  9 cm dish: 5 ml (out of 9 ml) is replaced by 5 ml fresh PM1 medium As soon as the first cell divisions were observed (2 to 4 cell stage) the culture medium was replaced by PM2 medium, also this medium is partly replaced on a weekly basis as described above.

Calli of 2 mm diameter were placed on solid CRM medium at 1000 lux. As soon as the calli turn green the amount of light was increased to approx. 1700 lux. Calli without shoots were transferred to fresh CRM medium every three weeks.

Emerging shoots were cut from the calli, leaving behind as much callus as possible, and placed on MS30-gelrite medium either in jars or petridishes. To promote rooting, shoots were cut—to remove any residual callus- and transferred to fresh MS30-gelrite medium.

Example 6b

Embedded in Alginate

Starting with the fused protoplasts as described in example 5, protoplasts were resuspended in solution A; per tube containing $1\times10^6$ protoplasts. To each tube, 2.5 ml solution A was added; after carefully re-suspending the cells, 2.5 ml sodium alginate solution was added. Drops of 1 ml suspension were placed on solid medium B. After 1 hour the solidified medium including the protoplasts were rinsed with PM1 medium and transferred to dishes containing 3 resp. 6 ml PM1 medium (petri dishes of 6 or 9 cm diameter, respectively). Further media changes were similar as described in example 6a.

As soon as the calli reach a diameter of 2 mm, the alginate matrix was dissolved by replacing the culture medium by 50 mM sodium citrate solution. Each alginate disc was cut in 8 pieces and the dishes are placed on an orbital shaker for 2 hours (30 rpm).

Microcalli were collected using a pipette and transferred to a test tube. To this tube PM2 medium was added to a final volume of 10 ml and then the tube is centrifuged for 5 minutes at 60*g.

After washing with PM2 medium twice, calli were placed on CRM medium at 1000 lux; calli which turned green were grown further at 1700 lux. Calli were kept on this medium and transferred, if necessary, to fresh CRM medium every three weeks.

Shoots which emerged on these calli were cut from the callus and placed on MS30-gelrite medium, either in petri dishes or glass jars, shoots were transferred on fresh medium of the same composition until roots were formed. Rooted plants were placed on MS30 medium.

Example 7

Determination of Ploidy Level

From plants resulting from cell fusion or crosses between *Cichorium* and *Lactuca* plants, the relative ploidy level was determined. To this end, a small piece of leaf tissue 1 $cm^2$ was taken from the plants examined and chopped with a razor blade in CyStain® UV Ploidy buffer (Partec, Munster, Germany).

After filtration, the ploidy level of the sample was determined using a Partec PA flow cytometer and compared to the result of samples from *Cichorium* and *Lactuca* plants. Only diploid plants, resulting from cell fusion were retained.

Plants resulting from crosses between *Cichorium* and *Lactuca* sp. possess a ploidy level intermediate between *Cichorium* and *Lactuca* sp. (FIGS. 1A-1D).

Example 8

Molecular Characterization Genomic DNA

Resulting from the cross between *Cichorium* (ID=P155) and *Lactuca* (ID=P157), several seeds were harvested, of which three germinated seeds were analyzed as described in example 7 and identified as hybrid plants. To further characterize these plants, a molecular analysis was performed.

From these putative hybrid plants and both parents DNA was isolated, following a standard isolation procedure, starting with leaf explants of ±0.3 $cm^2$.

On this isolated DNA, a RAMP analysis was performed with two primers generating polymorphisms between *Cichorium* and *Lactuca*. The result showed unequivocally that the hybrid plant harbored genomic DNA of both parents, thus demonstrating this plant was indeed a genomic hybrid between *Cichorium* and *Lactuca*.

Primers used for the reaction were:

Bejop09631    AGTCGGGTGG    (SEQ ID No. 37; RAPD primer)

Bejop01751    CCAGGTGTGTGTGTGT    (SEQ ID No. 38; iSSR primer)

PCR conditions:
2 minutes 93° C.
40 cycles of: 30 s. 93° C.-30 s. 35° C.-90 s. 72° C.
5 minutes 72° C.
Heating is performed with 0.3° C./sec.

Example 9

Polyacrylamide Gel Electrophoresis

To analyze the RAMP patterns a "Gene ReadIR 4200 DNA analyzer" (Licor Inc.) was used. Based on an optimal concentration of 6.5% acrylamide DNA fragments differing 1 base pair in size can be separated. To envisage these fragments labeled (IRDye labels) primers were used, one third of the amount of forward primer was replaced by a labeled, identical primer.

The result showed unequivocally that the obtained plants harbored genomic DNA of both parents, thus demonstrating these three plants (H1 to H3) were indeed hybrids between *Cichorium* and *Lactuca* (FIG. 2).

Example 10

Characterization of Mitochondrial DNA of the Selected Fusion Plant

Mitochondrial DNA was characterized to demonstrate that indeed the cytoplasm of *Cichorium* was replaced by the *Lactuca* cytoplasm.

Buffers used were essentially as described. However, some buffers were adjusted as denoted in the section "Solutions and chemicals". All experimental steps were performed with precooled buffers and at 4° C., unless stated otherwise.

100 grams of fresh leaves were homogenized on ice with a blender in 250 ml GB buffer. The homogenate was vacuum filtered on 4 layers of cheesecloth and 2 layers of nylon mesh (75 μm). The residue was homogenized further using a precooled mortar and pestle and subsequently filtered as described.

Filtrates were pooled and centrifuged for 10 minutes at 1.000×g; the supernatant was re-centrifuged at 2.000×g. Finally mitochondria were collected by centrifugation at 16.000×g. The resulting pellet was resuspended using a paint brush in 10 ml DNAse storage buffer.

Following centrifugation at 2.000×g, the resulting supernatant was pipetted to a centrifuge tube, 50 μl 2M $MgCl_2$ and 200 μl 5 mg/ml DNAse were added. After incubation for one hour, 20 ml of shelf buffer was pipetted under this mixture.

After centrifugation at 14.000×g, the resulting pellet was resuspended in 10 ml shelf buffer. The suspension was centrifuged for 10 minutes at 16.000×g, the pellet was dissolved in 600 μl Lysis Buffer and transferred to a 1.5 ml Eppendorf test tube. In this lysate, containing the mitochondrial DNA, 1 mg proteinase K is dissolved and 10 μl RNAse-A solution was added. Incubation was first 60 minutes at 37° C. followed by 30 minutes incubation at 65° C.

After this incubation, DNA was precipitated by adding 200 μl 5 M KAc and mixed by turning over the test tube, leaving it then for maximum 15 minutes on ice. Next is a centrifugation during 10 minutes at 20.000×g at room temperature. Finally, the DNA is subsequently extracted with phenol/chloroform/isoamylalcohol and chloroform/isoamylalcohol. The remaining water phase was mixed with 400 μl isopropanol and 27 μl 7.5 M ammoniumacetate.

After centrifugation for 10 minutes at 20.000×g (20° C.) the remaining pellet was washed with 500 μl 70% ethanol in water and re-centrifuged for 2 minutes at 20.000×g (20° C.) After drying the resulting DNA is dissolved in 200 μl TE buffer.

A second DNA precipitation was performed by adding 20 μl 7.5 M Na-Acetate and 150 μl isopropanol, the mixture was mixed gently for a few seconds.

The next centrifugation is 10 minutes at 20.000×g (20° C.). The pellet was washed with 500 μl 70% ethanol in water and re-centrifuged shortly (2 minutes at 20.000×g (20° C.). The pellet was dried and dissolved in 22 μl sterile ultrapure water. Storage was at 4° C.

Purity and concentration of the DNA was determined using a Nanodrop 2000 Spectrophotometer, a Qubit 2.0 Fluorometer and standard agarose gel electrophoresis techniques.

The sequence of the isolated mitochondrial DNA was determined by Next Generation sequencing using sequencing techniques generally known to the person skilled in the art.

This sequencing resulted in the identification of several regions where the mitochondrial DNA (mtDNA) of the selected CMS *Cichorium* plant equals either the original fertile *Cichorium* plant or the *Lactuca* donor, proving the mitochondrial DNA of the selected CMS *Cichorium* plant to be a rearrangement of the mtDNA of both the original fertile *Cichorium* plant and the *Lactuca* donor.

To this end, 4 sets of PCR primers were developed to identify the unique rearranged mtDNA of the selected fusion plant leading to the CMS phenotype. Also a set of 17 SNPs were developed as a further characterization of the selected fusion product (Table 2). From this data it is concluded that the selected CMS *Cichorium* plant contains an unique rearranged mitochondrial DNA with fragments of both parent lines being responsible for the CMS character of the described plant. Experimental details are shown in the tables mentioned above.

TABLE 1

Data for PCR reactions discriminating between both fusion parents and the selected CMS *Cichorium*

| Primer combination | Forward primer sequence | Reverse primer sequence | *Lactuca* | Fertile *Cichorium* | CMS *Cichorium* | Fragment size |
|---|---|---|---|---|---|---|
| 1 | SEQ ID 29 | SEQ ID 30 | − | + | + | 611 bp |
| 2 | SEQ ID 31 | SEQ ID 32 | + | − | + | 1592 bp |

TABLE 1-continued

Data for PCR reactions discriminating between both fusion parents and the selected CMS Cichorium

| Primer combination | Forward primer sequence | Reverse primer sequence | Lactuca | Fertile Cichorium | CMS Cichorium | Fragment size |
|---|---|---|---|---|---|---|
| 3 | SEQ ID 33 | SEQ ID 34 | + | − | + | 293 bp |
| 4 | SEQ ID 35 | SEQ ID 36 | − | + | + | 107 bp |

SEQ ID 29: GCCTCCAGGGTATGATCCTTAA
SEQ ID 30: CGAGCACTTATTTGACCTGTGT
SEQ ID 31: TGCTAACGAGGTTCAATGATG
SEQ ID 32: TTCGATTCAGGATCAAGCCCAG
SEQ ID 33: TCGATATTCTTTTCGCGACAGG
SEQ ID 34: TTAGGTTATTTCGTTGGTCGCC
SEQ ID 35: TTTATAGACAGCGACTCCCTCC
SEQ ID 36: ACCTGAAGGGAGTTATGGCATT

PCR conditions for this reaction were as follows:
total DNA was isolated from young leaf tissue as described and treated with RNAseA/T1. DNA integrity was confirmed by agarose gel electrophoresis. DNA from all samples was diluted to 15 ng/µl for PCR reactions. The amount of template DNA was 15 ng per PCR reaction. PCR for both marker combinations was carried out using Biomix Red (GC Biotech) in 20 µl reactions with 10 pmol of each primer mentioned above. PCR parameters were:

1 minute 94° C.
30 cycles of: 15 s. 94° C.; 15 s. 58° C.; 1 minute 72° C.)
5 minutes 72° C.
Store at 4° C.

Five µl of the PCR reactions were loaded on a 1% agarose gel and separated using standard techniques, known to the person skilled in the art.

TABLE 2

Sequence of the 17 SNP markers developed to discriminate between both fusion parents and the selected fusion plant. Denoted are the sequences used and between brackets ( [N/N] ) is the single nucleotide differing between the plants as elucidated in the three columns right of this sequence. Analysis was performed bp LGC Genomics, see www.lgcgenomics.com

| SNP SEQ ID | Sequence | Lactuca | Fertile Cichorium | CMS Cichorium |
|---|---|---|---|---|
| 1 | CCGAACCGCGCGAAATGGTCGCCTATTACACGGCTCACTAACTCTGCCTG[G/T]AGTGGTGGTACCTATTATTCGTCGGCGGGGCGGTCCGGCGATAC | G | T | G |
| 2 | CICTTAAGGTTAGTTCTATGCCTCACAACAACTACCTCATAGGTGATTCT[A/C]AATCCGTCTTTAGATCAGAAGTAGATGCCTCTTCCAGGGCTCTGT | A | C | A |
| 3 | GTACCAAATGCTTGGCAATCCTTGGTAGAGCTTATTTATGATTTCGTGCT[G/T]AACCTGGTAAACGAACAAATAGGGGGICTTTCCGGAAATGTTAAA | T | G | T |
| 4 | TATTGATTACACTCCTTCTCCTACTGCTTCTCCTTATACCCACTAATGTT[A/C]TTCTTCGTCCTACCTTGACTATTGGGAAATTTCCATTCGAGAAAG | C | A | C |
| 5 | TGCAGCGTAAACTCCTGCTAAATGAATGCCTTTGCTTTGGCTTTGAAATT[A/C]TGTTCCTGATTCAACTCCTTCATGCCATTGATTGATGCAAGTCTT | A | C | A |
| 6 | CTGAATGACCTCTCTCATCTAATCGATCGGTGAAGGATGTCTTTGAAGAT[A/C]ATCTGGTCTGGCTCGTTACCATTAGTTCCTCTCTCTATAGTCGAG | A | C | A |
| 7 | CTCTTGTTCTCTTTTCTTAGTTAGGCCCAAGAAAGTACAAGATATAGCTT[G/T]ACTAATATACTAAGATGATAGCTAGAGACTAGAGATGAGAGTGCA | G | T | G |
| 8 | TIGGATATTGTACGACAGGATCCCCATCCGTGTTTTCGTTTCGCTAACGA[G/T]AAAGGCCGGAAAGCGTGGGACCTATTTAAGTGACCTGGCCGATGG | G | T | G |
| 9 | TTTTTCGTTCCTTCTCTTCGATAAGAATATCGATTTGAAATGATAAAAAT[G/T]CCTCTTTATTCTCTTGTGCTCAGCGAAAGAACTGCCTAAGCATAC | G | T | G |
| 10 | GTCCGATCGTCGCTAGAGGCCCGTCGACTATAATACACTGTTCGAAATTT[A/C]TTCGTTTCTGCCGAAACAAAACGGGATTGGCTATCTTAACCTTAG | A | C | A |
| 11 | AAGGAAATGATCTTTACATGGAAATGAAAGAATCTGGAGTAATTAATGAA[A/C]AAAATATTCCAGAATCAAAAGTAGCTCTAGTTTACGGTCAGATGA | A | C | C |
| 12 | GGGGCGTCCAAAGAGTCGATCATTTCTGCATGATTTTTTTCTCGTGCACT[A/G]CCCCTTCCAATGGGTTTCGAAGATAAAAATCCTTTATTGGCCCAT | A | G | G |

TABLE 2-continued

Sequence of the 17 SNP markers developed to discriminate
between both fusion parents and the selected fusion plant.
Denoted are the sequences used and between brackets ( [N/N] )
is the single nucleotide differing between the plants as
elucidated in the three columns right of this sequence.
Analysis was performed bp LGC Genomics, see
www.lgcgenomics.com

| SNP SEQ ID | Sequence | Lactuca | Fertile Cichorium | CMS Cichorium |
|---|---|---|---|---|
| 13 | CATACGCTAAAATTTGTCCCTTTTTAATGCATTTACCCCGCTGAACCTGG[A/G]GTTITTGATGCATACAAGTATTTTTGTTGGAACGTTGATACATAA | G | A | A |
| 14 | AGATAAAAATAACAAGGAATAGAATTTGATTAGTTGGTATTCAAAATATA[C/T]GATTCAAGTAGTCAAGTCGAGAAAGAGATGGTTGAATCAAAATAA | T | C | C |
| 15 | TAAGCAATATATTGATTTTCTTCTCCAGGAACAGGCTCGATTCCATAGCA[G/T]CGCCCTTTGTAACGATCAAGGCTCGTAAGTCCATCGGICCACACA | T | G | G |
| 16 | ACTTTTTATTGGCATTGGAAGCACATTACATTATGGCAGGGTAATGTTTC[A/G]CAGTTTAATGAATCTTCCACTTATTTGATGGGCTGGTTAAGAGAT | G | A | A |
| 17 | GGTATGAATAGTTTATCAGTCTGGGCATGGATGTTTTTATTTGGACATCT[G/T]GTTTGGGCTACTGGATTTATGTTTTTAATTTCCTGGCGTGGATAT | G | T | T |

Example 11

Characterization of Pollen Grains

To illustrate the difference between the original fertile chicory plant and the selected fusion plant, a study was made of the available pollen grains. Studying the selected fusion plant P153, putative pollen grains were visible, however, both an attempted self-fertilization and a stain with FDA (Example 3) showed this putative pollen was not functional.

Further testing of the pollen of *Cichorium* and the selected fusion plant learned that from the latter pollen grains were significantly smaller. Pollen grains, suspended in WS9M, were imaged using regular bright field techniques on an inverted microscope with a 10× objective lens and recorded with a 3 MB CCD camera. Digital images of pollen grains were processed and analyzed using ImageJ software (Rasband, W. S., ImageJ, U. S. National Institutes of Health, Bethesda, Md., USA, http://imagej.nih.gov/ij/, 1997-2012).

Images were converted into 8-bit binary images. Holes were closed, dark outliers were removed (radius=10 pixels), and pollen grain projections touching each other were separated using the "watershed" command. The resulting images were analyzed with the "analyze particles" command to obtain the surface areas of the pollen grain projections. Objects touching the edge of the image were excluded. Using Microsoft Excel statistical functions, the measurements were converted into μm$^2$ and averaged.

For the selected fusion plants pollen surface varied between 1150 and 1850 μm$^2$ (SD=180), for the original *Cichorium* plant pollen grains, the determined surface was between 1550 and 2550 μm$^2$ (SD=226). Furthermore, student T-test analysis indicated that the chance that both populations of pollen grains are equal is below 0.01 (FIG. 3).

Solutions and chemicals.
Unless stated otherwise all solutions were autoclaved
(20 minutes at 120° C.)

|  | ½MS15 | MS30 | MS30-gelrite |
|---|---|---|---|
| ½MS medium Duchefa; M0233 | 2.28 g/l | — | — |
| MS medium Duchefa; M0222 | — | 4.40 g/l | 4.40 g/l |
| Sucrose | 15 g/l | 30 g/l | 30 g/l |
| Agar Duchefa; M1002 | 7 g/l | 7 g/l | — |
| Gelrite Duchefa; G1101 | — | — | 7.5 g/l |
| pH | 5.8 | 5.8 | 5.8 |

| WS9M medium | |
|---|---|
| $KH_2PO_4$ | 0.20 mM |
| $CaCl_2 \cdot 2H_2O$ | 10 mM |
| $KNO_3$ | 1 mM |
| $MgSO_4 \cdot 7H_2O$ | 1 mM |
| MES (monohydrate) | 2.8 mM |
| Mannitol | 0.5M |
| pH 5.6; 580 mOsm/kg | |

| enzyme solution: | |
|---|---|
| WS9M medium supplemented with: | |
| Yakult Cellulase Onozuka R10 | 0.2% (w/v) |
| Pectinase (Sigma, P4300) | 0.2% (w/v) |
| pH 5.6-5.7, filter sterile | |

| wash solution: | |
|---|---|
| $CaCl_2 \cdot 2H_2O$ | 13.6 mM |
| KCl | 0.34M |
| MES (monohydrate) | 2.8 mM |
| pH 5.8; 640 mOsm/kg | |

60 mM IOA stock solution:

| | |
|---|---|
| 0.222 g | IOA per 20 ml wash solution |

PEG1500 solution:

| | |
|---|---|
| PEG1500 | 40% (w/v) |
| Glucose anhydrous (w/v) | 0.3M |
| $CaCl_2 \cdot 2H_2O$ | 50 mM |
| filter sterile | |

PEG diluting solution

| | |
|---|---|
| Glycine | 50 mM |
| glucose anhydrous | 0.3M |
| $CaCl_2 \cdot 2H_2O$ | 50 mM |
| pH 10.5; 520 mOsm/kg; filter sterile | |

$CPW-Ca^{++}$ solution 200 ml

| | |
|---|---|
| 10 × CPW salts stock (ref. 3) | 20 ml |
| $CaCl_2 \cdot 2H_2O$ | 50 mM |
| Mannitol | 0.365M |
| pH 5.7; 530 mOsm/kg; filter sterile | |

| Culture media | PM1 | PM2 |
|---|---|---|
| $KNO_3$ | 7.42 mM | — |
| $MgSO_4 \cdot 7H_2O$ | 0.69 mM | 0.69 mM |
| $CaCl_2 \cdot 2H_2O$ | 1.5 mM | 1.5 mM |
| $KH_2PO_4$ | 0.62 mM | 0.62 mM |
| KCl | — | 5 mM |
| Gamborg[4] B5 micro 100x stock | 5 ml/l | 5 ml/l |
| KI | 0.73 µM | 0.73 µM |
| FeNaEDTA | 0.11 mM | 0.11 mM |
| Gamborg B5 vitamins (Duchefa; G0415) | 11.2 mgram/l | 11.2 mgram/l |
| Glutamine | 2.57 mM | 5.14 mM |
| Sucrose | 14.6 mM | 14.6 mM |
| Mannitol | 0.41M | 0.30M |
| NAA | 10.2 µM | 2.5 µM |
| BA | 4.44 µM | — |
| Caseinehydrolysate (Duchefa; C1301) | — | 150 mgram/l |
| pH | 5.5-5.6 | 5.5-5.6 |
| osmolarity | 530 mOsm/kg filtersterile | 400 mOsm/kg filtersterile |

CRM medium

| | |
|---|---|
| MS medium (Duchefa; M0222) | 4.40 gram |
| Sucrose | 30 mM |
| Zeatin | 4.56 µM |
| BA | 2.22 µM |
| caseinehydrolysate (Duchefa; C1301) | 300 mgram/l |
| agar (Duchefa; M1002) | 8 gram/l |
| pH 5.7 | |

Sodium Citrate 50 mM:
Solution A, Sodium Alginate Solution, Medium B: Ref. 5
Gamborg B5 Media:

PCR mix:

| | |
|---|---|
| Tris-HCl (pH 8.8) | 75 mM |
| $NH_4SO_4$ | 20 mM |
| Tween20 | 0.01% (v/v) |
| $MgCl_2$ | 2.8 mM |
| dNTPs | 0.25 mM |
| forward primer | 0.15 µM |
| reverse primer | 0.2 µM |
| Red Hot ® DNA Polymerase (ABgene, Epsom U.K.) | 0.04 units/µl |
| genomic plant DNA | ~0.2 ng/µl |

GB (Grinding buffer)

| | |
|---|---|
| sorbitol | 0.35M |
| mannitol | 0.1M |
| Tris-HCl pH 7.6 | 50 mM |
| $Na_2$-EDTA | 5 mM |
| BSA | 0.2% (w/v) |
| PVP | 1.0% (w/v) |
| spermidine | 0.025% (w/v) |
| β mercaptoethanol | 0.125% (v/v) |
| DIECA | 10 mM |

DNase storage buffer:

| | |
|---|---|
| Sodiumacetate | 5M |
| $CaCl_2 \cdot 2H_2O$ | 1M |
| pH 4.5 using acetic acid; | |
| prior to use, an equal volume glycerol is added | |

DNase Buffer (DB) (4° C.)

| | |
|---|---|
| DIECA (add just prior to use) | 10 mM |

Shelf Buffer (SB)

| | |
|---|---|
| Sucrose | 0.6M |
| Tris HCl pH 7.2 | 10 mM |
| $Na_2$-EDTA | 20 mM |
| DIECA (add just prior to use) | 10 mM |

TE buffer

| | |
|---|---|
| Tris-HCl pH 7.5 | 50 mM |
| $Na_2$-EDTA | 10 mM |

5 mg/ml DNase in DNase storage buffer
2M $MgCl_2$
Proteinase K
RnaseA solution: Thermo Scientific productnr. EN0551
5M KAc
Phenol/chloroform/isoamylalcohol (25:24:1)
chloroform/isoamylalcohol (24:1)
7.5M $NH_4$-Acetate
7.5M Na-Acetate pH 4.5-5.2

ABBREVIATIONS

BA 6 benzylaminopurine
bp basepairs
BSA bovine serum albumin
CMS cytoplasmic male sterile cytoplasmic male sterility
DIECA Na-diethyldithiocarbamate
EDTA ethylene diaminetetra acetic acid
FDA fluorescein diacetate
IOA iodoacetamide
IA iodoacetate
MES 2-(N-morpholino)ethanesulfonic acid
mtDNA mitochondrial DNA
NAA 1-naphthaleneacetic acid
ng nanogram
PCR polymerase chain reaction
PEG polyethylene glycol
PVP polyvinylpyrrolidone
RAMP Random Amplified Microsatellite Polymorphism
SD standard deviation
SNP single nucleotide polymorphism
K G or T)
M A or C) nucleotide ambiguity codes
R G or A) according to the rules of IUPAC
Y T or C)

The invention claimed is:

1. Cytoplasmic male sterile *Cichorium intybus* plant comprising *Lactuca* mitochondria of a plant which was deposited with the NCIMB under accession number NCIMB 41985.

2. Cytoplasmic male sterile *Cichorium intybus* plant according to claim 1, wherein said cytoplasmic male sterile *Cichorium intybus* plant is further identifiable by a molecular marker of 1592 bp using nucleic acid amplification primers SEQ ID No. 31 and SEQ ID No. 32.

3. Cytoplasmic male sterile *Cichorium intybus* plant according to claim 1, wherein said cytoplasmic male sterile *Cichorium intybus* plant is further identifiable by a molecular marker of 293 bp using nucleic acid amplification markers SEQ ID No. 33 and SEQ ID No. 34.

4. Cytoplasmic male sterile *Cichorium intybus* plant according to claim 1, wherein said *Cichorium intybus* plant comprises a cytoplasm of a plant which was deposited with the NCIMB under accession number NCIMB 42125.

* * * * *